United States Patent
Tashima et al.

(10) Patent No.: US 12,386,087 B2
(45) Date of Patent: Aug. 12, 2025

(54) IMAGE PROCESSING DEVICE, IMAGE PROCESSING SYSTEM, AND IMAGE PROCESSING METHOD

(71) Applicants: National Institutes for Quantum Science and Technology, Chiba (JP); Atox Co., Ltd., Tokyo (JP)

(72) Inventors: Hideaki Tashima, Chiba (JP); Go Akamatsu, Chiba (JP); Taiga Yamaya, Chiba (JP)

(73) Assignees: National Institutes for Quantum Science, Chiba (JP); Technology Atox Co., Ltd., Tokyo (JP)

( * ) Notice: Subject to any disclaimer, the term of this patent is extended or adjusted under 35 U.S.C. 154(b) by 193 days.

(21) Appl. No.: 18/551,510

(22) PCT Filed: Mar. 22, 2022

(86) PCT No.: PCT/JP2022/012938
§ 371 (c)(1),
(2) Date: Sep. 20, 2023

(87) PCT Pub. No.: WO2022/202727
PCT Pub. Date: Sep. 29, 2022

(65) Prior Publication Data
US 2024/0168186 A1 May 23, 2024

(30) Foreign Application Priority Data
Mar. 22, 2021 (JP) ................ 2021-047690

(51) Int. Cl.
*A61B 6/03* (2006.01)
*G01T 1/167* (2006.01)
*G01T 1/29* (2006.01)

(52) U.S. Cl.
CPC ............ *G01T 1/2992* (2013.01); *A61B 6/037* (2013.01); *G01T 1/167* (2013.01); *G01T 1/2985* (2013.01)

(58) Field of Classification Search
CPC ..... G01T 1/2992; G01T 1/167; G01T 1/2985; A61B 6/037
See application file for complete search history.

(56) References Cited

U.S. PATENT DOCUMENTS

| | | | |
|---|---|---|---|
| 7,312,455 B2 * | 12/2007 | Manjeshwar | A61B 6/037 250/363.03 |
| 7,397,035 B2 | 7/2008 | Watson | |

(Continued)

FOREIGN PATENT DOCUMENTS

| | | |
|---|---|---|
| JP | 2019032211 A | 2/2019 |
| WO | 2018163362 A1 | 9/2018 |
| WO | 2019149621 A1 | 8/2019 |

OTHER PUBLICATIONS

EPO; European Search Report for corresponding European Patent Application No. 22775514.7, mailed Jan. 29, 2025, 8 pages.

(Continued)

*Primary Examiner* — David J Makiya
(74) *Attorney, Agent, or Firm* — NK Patent Law

(57) ABSTRACT

By a technique different from conventional techniques, quality of an image obtained by nuclear medicine imaging is improved. In an image processing device, a first reconstruction process section generates, by a reconstruction process with respect to list mode data acquired by a PET device, an initial image indicating a concentration distribution of a radioactive substance. A scatter component derivation section derives, from the initial image, scatter component projection data indicating a scatter component of radiation rays by scatter estimation simulation. A second reconstruction process section generates, by a reconstruction process with respect to the scatter component projection data, a low resolution scatter image indicating the scatter component and having a resolution lower than that of the initial image. An upscaling process section generates an upscaled scatter image having a resolution identical with that of the initial image by upscaling the low resolution scatter image.

9 Claims, 8 Drawing Sheets

(56) References Cited

U.S. PATENT DOCUMENTS

| | | | |
|---|---|---|---|
| 8,265,365 B2 * | 9/2012 | Panin | G06T 11/005 |
| | | | 382/128 |
| 2018/0203140 A1 | 7/2018 | Miao | |
| 2019/0197674 A1 * | 6/2019 | Bai | G06T 11/008 |
| 2020/0012002 A1 | 1/2020 | Kobayashi | |

OTHER PUBLICATIONS

C.C. Watson, "New, Faster, Image-Based Scatter Correction for 3D Pet", IEEE Transactions on Nuclear Science, vol. 47, No. 4, dated Aug. 2000, pp. 1587-1594, XP002323734, CTI PET Systems, Inc. Knoxville, TN, US.

Hideaki Tashima, et al., "First prototyping of a dedicated PET system with the hemisphere detector arrangement", Phys. Med. Biol. 64, Mar. 8, 2019, 065004, 13 pages, Tokyo Japan, XP093238837.

ISA/JP; International Search Report and Written Opinion for corresponding International Patent Application No. PCT/JP2022/012938, mailed Jun. 14, 2022, 6 pages.

Tashima, Hideaki et al.; Abstract of "Development of Reconstruction Method for the Helmet PET", 2016, 4 pages.

\* cited by examiner

IMAGE PROCESSING DEVICE, IMAGE PROCESSING SYSTEM, AND IMAGE PROCESSING METHOD

CROSS-REFERENCE TO RELATED APPLICATIONS

This application is a U.S. National Stage Application of International Patent Application No. PCT/JP2022/012938, filed on Mar. 22, 2022, which claims priority to Japanese Patent Application No. 2021-047690, filed on Mar. 22, 2021, the entire contents of all of which are incorporated by reference herein.

TECHNICAL FIELD

An aspect of the present invention relates to an image processing device that processes an image obtained by nuclear medicine imaging.

BACKGROUND ART

In recent years, various techniques related to nuclear medicine imaging have been proposed. For example, Patent Literature 1 discloses a technique for improving quality of an image obtained by positron emission tomography (PET), which is an example of a nuclear medicine imaging technique (a specific technique in Patent Literature 1 will be described later).

CITATION LIST

Patent Literature

[Patent Literature 1]
U.S. Pat. No. 7,397,035 B2

SUMMARY OF INVENTION

Technical Problem

An object of an aspect of the present invention is to improve, by a technique different from conventional techniques, quality of an image obtained by nuclear medicine imaging.

Solution to Problem

In order to attain the object, an image processing device in accordance with an aspect of the present invention includes: a first reconstruction process section that generates, by a reconstruction process with respect to list mode data pertaining to a subject, an initial image indicating a concentration distribution of a radioactive substance in the subject, the list mode data having been acquired by a nuclear medicine imaging device; a scatter component derivation section that derives, from the initial image, scatter component projection data by scatter estimation simulation, the scatter component projection data indicating a scatter component of radiation rays radiated from the radioactive substance; a second reconstruction process section that generates a low resolution scatter image by a reconstruction process with respect to the scatter component projection data, the low resolution scatter image indicating the scatter component and having a resolution lower than that of the initial image; an upscaling process section that generates an upscaled scatter image by upscaling the low resolution scatter image, the upscaled scatter image having a resolution identical with that of the initial image; and an image correction section that generates a scatter-correction image by subtracting the upscaled scatter image from the initial image.

Moreover, an image processing method in accordance with an aspect of the present invention is an image processing method in which steps are carried out by a computer, the method including: a first reconstruction process step of generating, by a reconstruction process with respect to list mode data pertaining to a subject, an initial image indicating a concentration distribution of a radioactive substance in the subject, the list mode data having been acquired by a nuclear medicine imaging device; a scatter component derivation step of deriving, from the initial image, scatter component projection data by scatter estimation simulation, the scatter component projection data indicating a scatter component of radiation rays radiated from the radioactive substance; a second reconstruction process step of generating a low resolution scatter image by a reconstruction process with respect to the scatter component projection data, the low resolution scatter image indicating the scatter component and having a resolution lower than that of the initial image; an upscaling process step of generating an upscaled scatter image by upscaling the low resolution scatter image, the upscaled scatter image having a resolution identical with that of the initial image; and an image correction step of generating a scatter-correction image by subtracting the upscaled scatter image from the initial image.

Advantageous Effects of Invention

According to an aspect of the present invention, it is possible to improve, by a technique different from conventional techniques, quality of an image obtained by nuclear medicine imaging.

DESCRIPTION OF EMBODIMENTS

Embodiment 1

Figure 1:
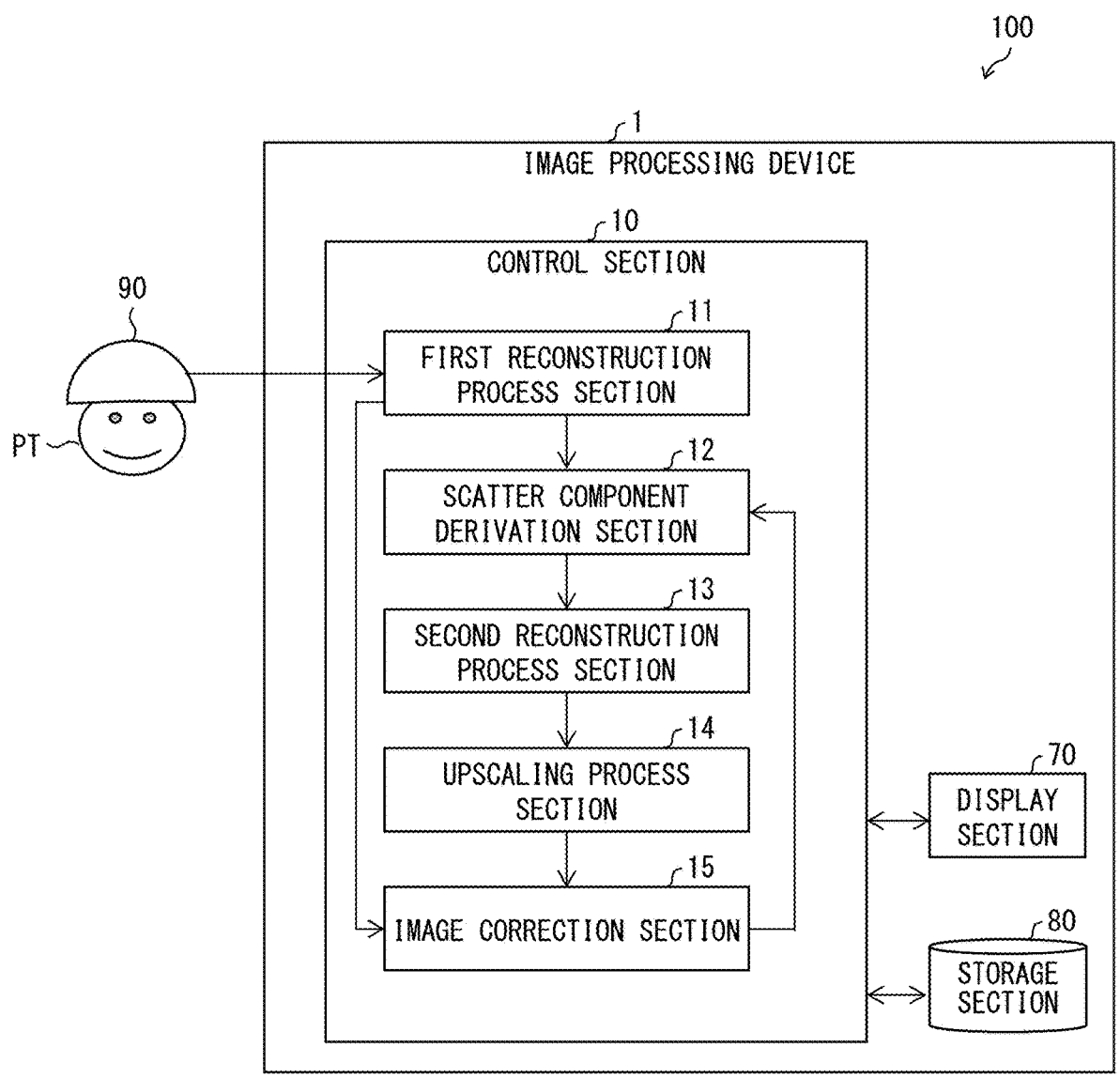
FIG. 1 is a diagram illustrating a main part configuration of an image processing system in accordance with Embodiment 1.

The following description will discuss details of an image processing system 100 in accordance with Embodiment 1. For convenience of explanation, constituent elements (components) identical in function to those described in Embodiment 1 are given identical reference numerals, and descriptions of such constituent elements will not be repeated in the subsequent embodiments. Moreover, for simplification, descriptions of matters similar to those of publicly known techniques will be omitted as appropriate.

Note that configurations and numerical values described herein are mere examples, unless otherwise specified. Therefore, unless otherwise specified, positional relations of constituent elements are not limited to examples in the drawings. Moreover, it should be noted that the drawings are intended to schematically explain shapes, structures, and positional relations of constituent elements, and that the drawings are not necessarily drawn to conform to actual cases. In this specification, descriptions of "A to B" related to two numerals A and B mean "A or more and B or less" unless otherwise specified.

(Schematic Description of PET)

In PET, a chemical agent labeled with a positron-emitting nuclide is injected (administered) into a subject (subject to be imaged), and a distribution of the chemical agent in the subject is imaged. In PET, a pair of radiation rays (annihilation radiation) emitted from the administered chemical agent in directions of approximately 180° are measured by coincidence counting of detectors arranged to surround the subject. In PET, time series data (coincidence data) obtained by coincidence counting is referred to also as list mode data. In PET, an image (reconstructed image) indicating a concentration distribution (hereinafter, referred to simply as "concentration distribution") of a radioactive substance in a subject is generated (derived) by a reconstruction process with respect to the list mode data. The reconstructed image is typically a three-dimensional image.

Note, however, that the coincidence data includes "scatter coincidence data" in addition to "true coincidence data". The scatter coincidence data is data which is measured when one or both of a pair of emitted radiation rays are scattered in a subject. The scatter coincidence data is noise data, and therefore deteriorates quality (image quality) of a reconstructed image.

Therefore, various techniques have been proposed in order to improve quality of a reconstructed image. For example, Patent Literature 1 proposes a scatter-correction technique using the single scatter simulation (SSS) method, which is one of scatter estimation simulation techniques. The SSS method is a technique for estimating, on a projection data space, a scatter component of radiation rays on the assumption that the radiation rays are scattered only once, based on a concentration distribution and an attenuation coefficient distribution.

In the technique of Patent Literature 1, scatter component projection data (which is data indicating a scatter component of radiation rays) is derived from a reconstructed image using the SSS method. The scatter component projection data can also be expressed as data obtained by coarse sampling. Then, the scatter component projection data is converted into interpolated list mode data by an interpolation process. Subsequently, initial list mode data (original list mode data) is corrected using the interpolated list mode data. By carrying out a reconstruction process with respect to the corrected list mode data (list mode data after correction), a reconstructed image is obtained in which influence of the scatter component is reduced. As such, Patent Literature 1 proposes a technique of improving quality of a reconstructed image by carrying out correction with respect to list mode data (i.e., by carrying out correction on a data space).

In contrast, the inventors of the present application (hereinafter, referred to simply as "inventors") have newly found, as a result of diligent studies, that it is possible to improve quality of a reconstructed image by a technique different from conventional techniques. The inventors have newly created an image processing system 100 (in particular, an image processing device 1) based on such new findings.

(Configuration of Image Processing System 100)

FIG. 1 is a diagram illustrating a main part configuration of the image processing system 100. The image processing system 100 includes an image processing device 1 and a PET device 90. The image processing device 1 and the PET device 90 are communicably connected to each other through a known communication interface (not illustrated).

The image processing device 1 includes a control section 10, a display section 70, and a storage section 80. The control section 10 comprehensively controls components included in the image processing device 1. The display section 70 displays various images (e.g., various images generated by the image processing device 1). The storage section 80 stores various kinds of data and programs which are used in processes carried out by the control section 10.

Embodiment 1 employs the PET device 90 as an example of the nuclear medicine imaging device in accordance with an aspect of the present invention. FIG. 1 illustrates a helmet type PET device 90. The PET device 90 includes a helmet portion (hemispherical gantry) that can be brought closer to a head of a patient PT. The patient PT is an example of the subject in accordance with an aspect of the present invention. In the helmet portion, a plurality of detectors (not illustrated) are disposed along a housing of the helmet portion. The PET device 90 further includes a coincidence circuit (not illustrated) that acquires list mode data based on detection results of the detectors. The PET device 90 transmits the list mode data to the image processing device 1 (more specifically, to the control section 10).

The PET device 90 in the example illustrated in FIG. 1 is an example of a time-of-flight (TOF)-PET device, and is an example of a proximity type PET device. Note, however, that, as is clear for a person skilled in the art, the PET device in accordance with an aspect of the present invention is not limited to the helmet type PET device. Therefore, it should be noted that the PET device in accordance with an aspect of the present invention is not limited to the TOF-PET device and the proximity type PET device.

(Example of Process Flow of Image Processing Device 1)

Figure 2:
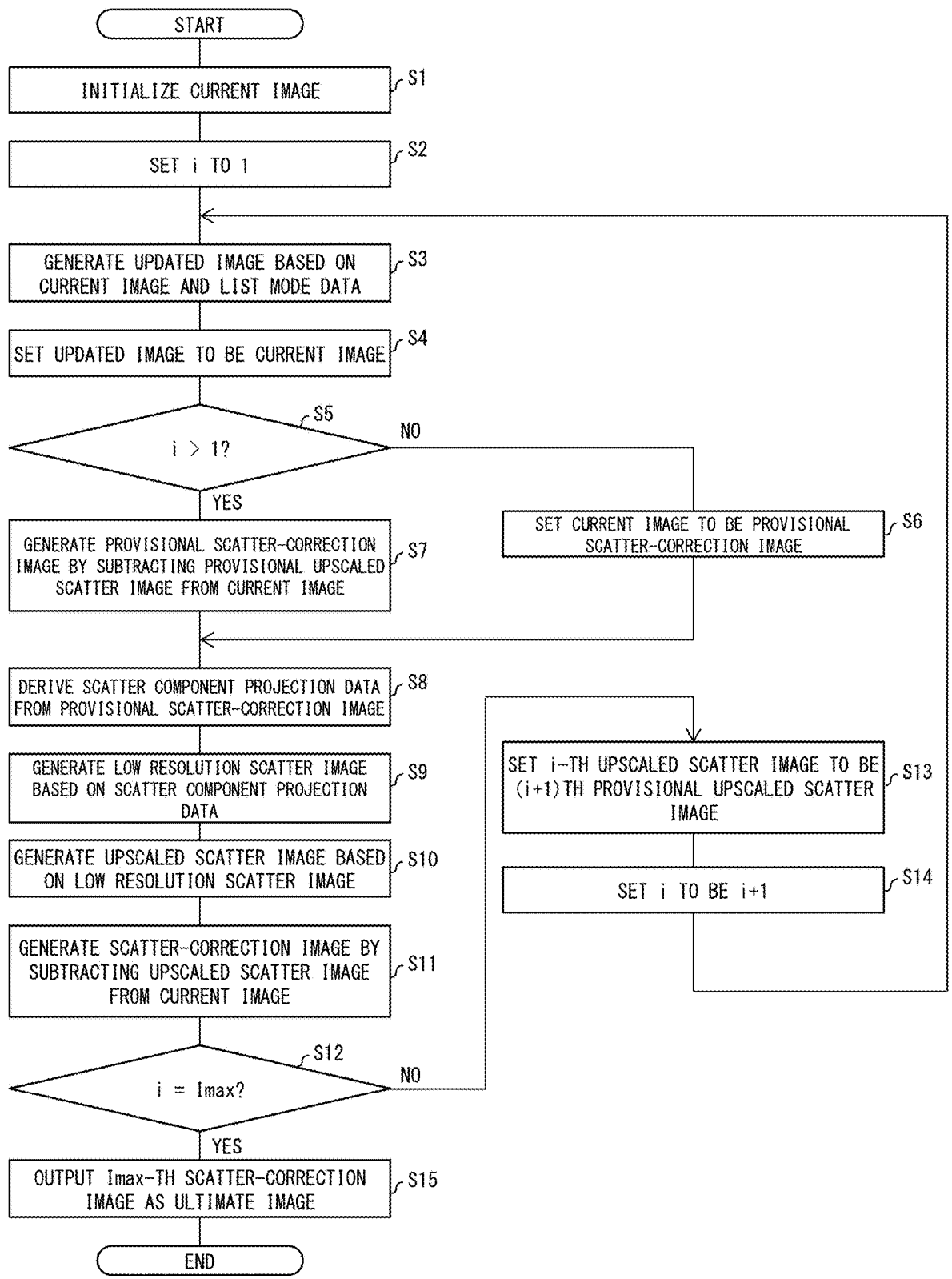
FIG. 2 is a diagram illustrating an example of a process flow of an image processing device in accordance with Embodiment 1.
Figure 3:
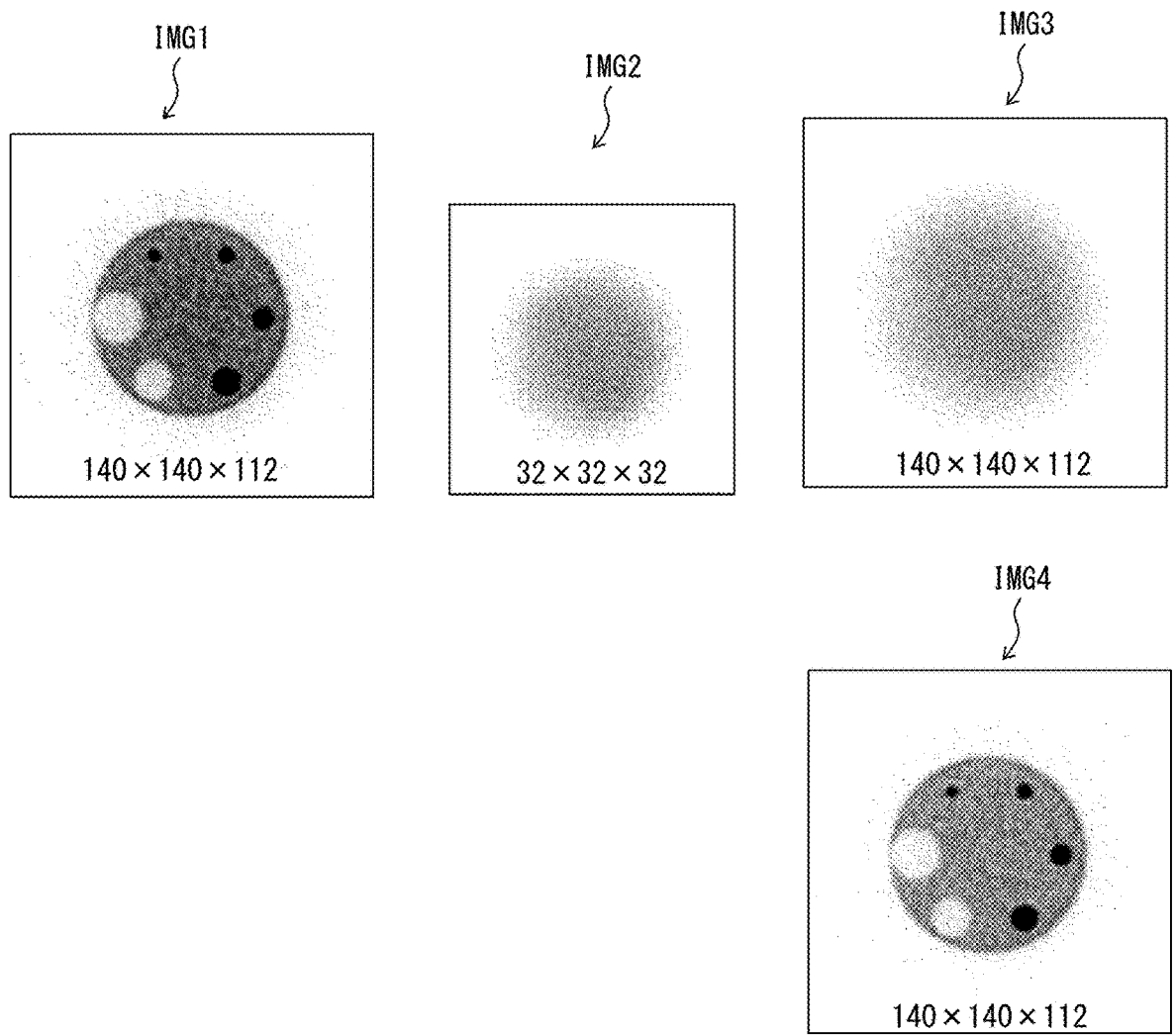
FIG. 3 is a diagram showing an example of images generated by the image processing device in accordance with Embodiment 1.

The image processing device 1 includes a first reconstruction process section 11, a scatter component derivation section 12, a second reconstruction process section 13, an upscaling process section 14, and an image correction section 15. FIG. 2 is a diagram illustrating an example of a process flow of the image processing device 1. FIG. 3 is a diagram showing an example of images generated by the image processing device 1.

In FIG. 2, Imax represents a predetermined number which is the maximum number of times a loop process illustrated in FIG. 2 is carried out. The number Imax can be expressed as an upper limit number of updates of a scatter-correction image. The number Imax can be set as appropriate by a user of the image processing device 1. For example, the number Imax can be set to 10. The following description will discuss an example case of Imax>2. Note, however, that the number Imax can be set to 1. The number Imax only needs to be an integer of 1 or more.

First, the first reconstruction process section 11 acquires list mode data pertaining to a subject from the PET device 90. Subsequently, the first reconstruction process section 11 initializes a current image (S1). For example, the image processing device 1 initializes all pixel values of the current image to 1. Note, however, that a method for initializing pixel values of a current image is not limited to the above example. For example, pixel values of a current image can be initialized with use of the number of pixels of the current image, the number of pieces of list mode data, and sensitivities associated with positions of respective pixels in an initial image.

Subsequently, the image processing device 1 sets a value i to 1 (initial value) (S2). The value i is a counter value (loop counter) indicating the number of times the loop process of FIG. 2 is carried out. Subsequently, the first reconstruction process section 11 generates an updated image based on the current image and the list mode data (S3). For example, the first reconstruction process section 11 may generate an updated image at i=1 by carrying out a reconstruction process with respect to the list mode data by a technique similar to Patent Literature 1. Then, the image processing device 1 sets the updated image to be the current image (S4).

In the case of i=1 in the process example of FIG. 2, the current image set in S4 is referred to also as an initial image. As described above, the first reconstruction process section 11 generates an initial image based on the list mode data. As is clear from the above descriptions, the initial image is an image indicating a concentration distribution of a radioactive substance in the subject. For example, a resolution (i.e., the number of pixels) of the initial image is 140 (horizontal resolution)×140 (vertical resolution)×112 (number of slices). The initial image may be referred to also as an image before scatter-correction. An image IMG1 in FIG. 3 is an example of the initial image generated by the first reconstruction process section 11.

In the descriptions below, a current image corresponding to the counter value i set in S4 is expressed also as IMGP(i). As described above, in the case of i=1, IMGP(1) is set to be IMG1.

Subsequently, the image processing device 1 determines whether or not the value i is greater than 1 (S5). In a case where the value i is 1 (No in S5), the image processing device 1 sets the current image (i.e., the initial image) to be a provisional scatter-correction image (S6). The provisional scatter-correction image may be referred to also as a current scatter-correction image. In a case of i>1 (Yes in S5), the process proceeds to S7. A technique for generating a provisional scatter-correction image in S7 will be described later.

Subsequently, the scatter component derivation section 12 derives scatter component projection data (which is data indicating a scatter component of radiation rays radiated from the radioactive substance) from the provisional scatter-correction image by, for example, a technique similar to Patent Literature 1 (e.g., using the SSS method) (S8). In a case of i=1, the scatter component derivation section 12 derives a scatter component projection data from the initial image.

Subsequently, the second reconstruction process section 13 generates a low resolution scatter image based on the scatter component projection data (S9). The low resolution scatter image is an image that indicates a scatter component of radiation rays radiated from the radioactive substance and that has a resolution lower than that of the current image (in other words, a resolution lower than that of the initial image). The low resolution scatter image may be referred to also as a small pixel number scatter image. Specifically, the second reconstruction process section 13 generates a low resolution scatter image by carrying out a reconstruction process with respect to the scatter component projection data. A reconstruction process technique in S9 can be similar to that in S3.

For example, the second reconstruction process section 13 generates the low resolution scatter image as an image having a resolution of 32×32×32. An image IMG2 in FIG. 3 is an example of the low resolution scatter image generated by the second reconstruction process section 13. As such, in Embodiment 1, the scatter component projection data is transformed into an image, instead of being converted into interpolated list mode data. In regard to this point, the process of Embodiment 1 is different from conventional techniques.

Subsequently, the upscaling process section 14 generates an upscaled scatter image based on the low resolution scatter image (S10). The upscaled scatter image in Embodiment 1 has a resolution identical with that of the current image (in other words, a resolution identical with that of the initial image). For example, the upscaling process section 14 generates an upscaled scatter image by upscaling, using a known technique, the resolution of the low resolution scatter image to a resolution identical with that of the current image. An image IMG3 in FIG. 3 is an example of the upscaled scatter image generated by the upscaling process section 14.

Subsequently, the image correction section 15 generates a scatter-correction image by subtracting the upscaled scatter image from the current image (S11). That is, the image correction section 15 generates an image IMGSC(i) as follows: IMGSC(i)=IMGP(i)−IMGUP(i). The image IMGSC(i) is a scatter-correction image corresponding to the counter value i. The image IMGUP(i) is an upscaled scatter image corresponding to the counter value i.

By generating the upscaled scatter image in S10 in advance, it is possible to carry out the subtraction process in S11 between two images having the same resolution. By this subtraction process, it is possible to remove a scatter component from the current image. That is, a scatter-correction image is generated as an image from which a scatter component has been removed from the current image. In a case of i=1, the image correction section 15 generates an image IMGSC(1) by subtracting the image IMGUP(1) from the image IMGP(1), which is the initial image.

Subsequently, the image processing device 1 determines whether or not the value i has reached Imax (S12). In a case where the value i has not reached Imax (No in S12), the image processing device 1 sets an i-th upscaled scatter image to be an (i+1)th provisional upscaled scatter image (S13). The provisional upscaled scatter image may be referred to also as a current upscaled scatter image. For example, in a case of i=1, the image processing device 1 sets the image IMGUP(i) to be a 2nd provisional upscaled scatter image. Then, the image processing device 1 increases the value i by 1 (S14). Subsequently, the process returns to S3.

In a case of i>1, the first reconstruction process section 11 generates an i-th (e.g., 2nd) updated image based on the current image ((i−1)th current image) generated in previous S4 and the list mode data. Then, in S4, the i-th updated image is set to be an i-th current image. Thus, in the process of FIG. 2, the current image is sequentially updated based on the list mode data. As described above, the first reconstruction process section 11 updates the current image related to the initial image based on the list mode data.

In a case of i>1 (Yes in S5), the image correction section 15 generates a provisional scatter-correction image by subtracting the provisional upscaled scatter image from the current image (S7). In other words, in the case of i>1, the image correction section 15 generates an i-th provisional scatter-correction image by subtracting an (i−1)th upscaled scatter image from the i-th current image.

As such, the current image is sequentially updated in accordance with an increase in the value i until the value i reaches Imax. Moreover, the processes of S3 through S14 are recursively repeated until the value i reaches Imax (i.e., until S12 is determined to be Yes). According to such a loop process, scatter components are sequentially removed from the current image in accordance with an increase in the value i.

The following description will discuss a main process in a current loop (i-th loop) in a case of 1<i≤Imax. First, in S8, the scatter component derivation section 12 newly derives scatter component projection data (i.e., updates scatter component projection data which has been derived in the previous loop) from a provisional scatter-correction image (i-th provisional scatter-correction image) in the current loop by scatter estimation simulation.

Subsequently, in S9, the second reconstruction process section 13 newly generates a low resolution scatter image (i.e., updates a low resolution scatter image generated in the previous loop) by carrying out a reconstruction process with respect to the scatter component projection data which has been updated in S8.

Subsequently, in S10, the upscaling process section 14 newly generates an upscaled scatter image (i.e., updates the upscaled scatter image generated in the previous loop) by upscaling the low resolution scatter image which has been updated in S9.

Subsequently, in S11, the image correction section 15 newly generates a scatter-correction image (i.e., updates the scatter-correction image generated in the previous loop) by subtracting the upscaled scatter image updated in S10 from the current image in the current loop.

After that, in a case where the value i has reached Imax (YES in S12), the image correction section 15 outputs, as an ultimate image, an Imax-th scatter-correction image (i.e., an ultimate scatter-correction image) (S15). For example, the image correction section 15 may output the ultimate image to the display section 70. An image IMG4 in FIG. 3 is an example of the ultimate image output by the image correction section 15. As is clear from the above descriptions, a resolution of the ultimate image is equal to the resolution of the initial image.

According to the process of FIG. 2, the ultimate image is obtained as an image from which scatter components included in the initial image i have been removed. In particular, by setting Imax to a large value, an ultimate image is obtained from which scatter components have been sufficiently removed. As described above, in Embodiment 1, it is possible to improve quality of a reconstructed image by carrying out correction to remove a scatter component in an image region, unlike conventional techniques.

Unlike the example of FIG. 2, in the image processing device 1, the upper limit number of updates (for convenience, referred to as Jmax) of an upscaled scatter image may be set to be smaller than the upper limit number of updates (i.e., Imax) of the current image. As such, in the process carried out by the image processing device 1, an update stop timing of an upscaled scatter image may precede an update stop timing of the current image. In this case, the image processing device 1 my generate scatter-correction images in respective subsequent loops with use of a lastly updated upscaled scatter image (i.e., an upscaled scatter image updated at a Jmax-th time).

(Verification Experiment 1)

The inventors have carried out an experiment (for convenience, referred to as "verification experiment 1") to verify effectiveness of the image processing technique (scatter-correction technique) in accordance with Embodiment 1. In the descriptions below, the scatter-correction technique of Patent Literature 1 and the scatter-correction technique of Embodiment 1 are referred to as the conventional technique and the present technique, respectively.

In verification experiment 1, an image quality evaluation phantom was used to evaluate uniformity (more specifically, uniformity of signal intensity in an image) of an image (PET image) obtained based on list mode data. The image quality evaluation phantom in verification experiment 1 was a cylindrical phantom having a diameter of 16.5 cm and a height of 14.1 cm. The image quality evaluation phantom was designed to be capable of being attached with six spheres (for convenience, referred to as "spheres through 6") having different diameters. The diameters of the spheres 1 through 6 were 10 mm, 13 mm, 17 mm, 22 mm, 28 mm, and 37 mm, respectively.

In verification experiment 1, $^{18}F$ radioactive solutions were enclosed in the spheres 1 through 4 and a background region, respectively, so that a radioactive concentration ratio between the spheres 1 through 4 and the background region was 4:1. In the spheres 5 and 6, water having no radioactivity was enclosed. Therefore, the spheres 1 through 4 may be referred to as hot spheres and the spheres 5 and 6 may be referred to as cold spheres (see also FIG. 4 described below).

While setting a timing at which a signal intensity (radioactive concentration) in the background region became 5.3 kBq/mL as a starting point, the image quality evaluation phantom was imaged using the PET device 90 over a period of 30 minutes. Then, images were generated by applying the conventional technique and the present technique, respectively, to the obtained list mode data.

Figure 4:
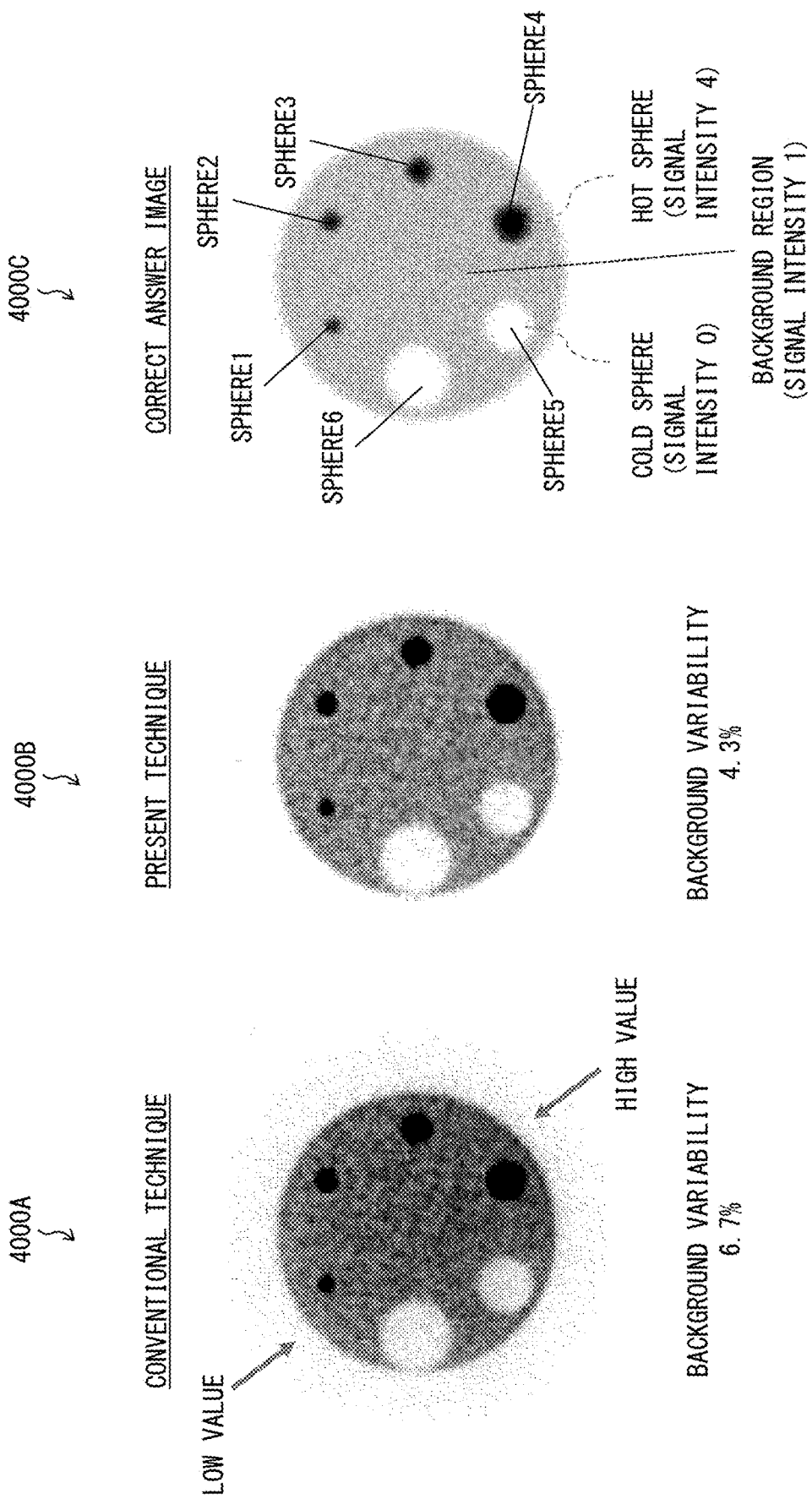
FIG. 4 is a diagram illustrating a result of verification experiment 1.

FIG. 4 is a diagram illustrating a result of verification experiment 1. Reference numerals 4000A, 4000B, and 4000C in FIG. 4 indicate (i) an image generated by the conventional technique (Comparative Example 1), (ii) an image generated by the present technique (Example 1), and (iii) a correct answer image (Correct Answer 1), respectively.

As illustrated in FIG. 4, nonuniformity of signal intensity in the background region was observed in Comparative Example 1. Specifically, in Comparative Example 1, (i) presence of a low value region was observed in the upper left of the background region, and (ii) presence of a high value region was observed in the lower right of the background region. Then, it was confirmed by the inventors that background variability in Comparative Example 1 was 6.7%.

In contrast, it was confirmed that nonuniformity of signal intensity in the background region was improved in Example 1, as compared with Comparative Example 1. Specifically, it was confirmed by the inventors that background variability in Example 1 was 4.3%. As described above, it was supported by verification experiment 1 that, according to the present technique, it is possible to obtain a high quality image as compared with the conventional technique.

(Verification Experiment 2)

Subsequently, the inventors further carried out a verification experiment (for convenience, referred to as "verification experiment 2"). In verification experiment 2, contrast of PET images was evaluated using a Hoffman brain phantom (which is an example of a phantom simulating a human brain). The Hoffman brain phantom was designed so that a signal intensity ratio (radioactive concentration ratio) between a spinal fluid region (simulated cerebrospinal fluid region), a white matter region (simulated cerebral white matter region), and a gray matter region (simulated cerebral gray matter region) was 0:1:4.

In verification experiment 2, 20 MBq of an $^{18}$F radioactive solution was enclosed in the Hoffman brain phantom. Then, the Hoffman brain phantom was imaged using the PET device 90 over a period of 30 minutes. Subsequently, images were generated by applying the conventional technique and the present technique, respectively, to the obtained list mode data, as with in verification experiment 1.

Figure 5:
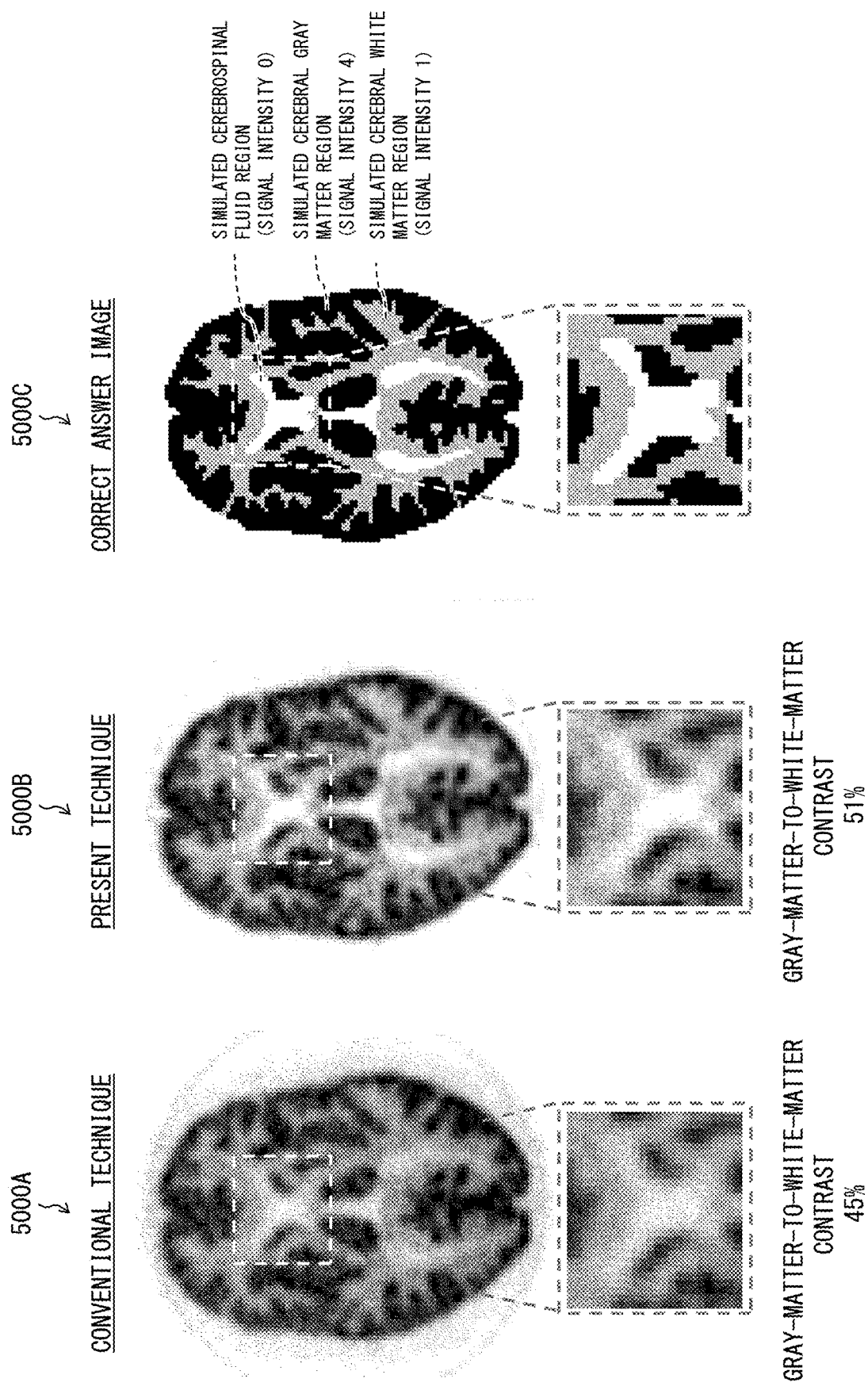
FIG. 5 is a diagram illustrating a result of verification experiment 2.

FIG. 5 is a diagram illustrating a result of verification experiment 2. Reference numerals 5000A, 5000B, and 5000C in FIG. 5 indicate (i) an image generated by the conventional technique (Comparative Example 2), (ii) an image generated by the present technique (Example 2), and (iii) a correct answer image (Correct Answer 2), respectively.

As illustrated in FIG. 5, in Comparative Example 2, it was confirmed that a gray color tone was attached (i.e., noise occurred) in the spinal fluid region (which should be displayed in white in a normal situation) in which the signal intensity should be 0 in a normal situation.

Subsequently, the inventors set regions of interest (ROI) in the gray matter region and the white matter region, and calculated gray-matter-to-white-matter contrast in the regions of interest. As a result, in Comparative Example 2, it was confirmed that the gray-matter-to-white-matter contrast was 45%. The gray-matter-to-white-matter contrast is one of index values for evaluating influence of the above described noise. In the absence of the noise, the gray-matter-to-white-matter contrast is 100%. Therefore, it can be said that, as the gray-matter-to-white-matter contrast increases, the noise is reduced.

In contrast, it was confirmed that the noise was reduced in Example 2, as compared with Comparative Example 2. Specifically, in Example 2, the spinal fluid region was displayed in a color tone closer to white, as compared with Comparative Example 2. Furthermore, in Example 2, it was confirmed that the gray-matter-to-white-matter contrast was 51%. As described above, it was supported also by verification experiment 2 that, according to the present technique, it is possible to obtain a high quality image as compared with the conventional technique.

A value of the ratio of the gray-matter-to-white-matter contrast (51%) in Experiment 2 to the gray-matter-to-white-matter contrast (45%) in Comparative Example 2 is approximately 1.13. Therefore, in verification experiment 2, it was confirmed that contrast of the image was improved by 13% by the present technique, as compared with the conventional technique.

(Effect)

As described above, according to the image processing system 100 (in particular, the image processing device 1), it is possible to improve, by a technique different from conventional techniques, quality of an image obtained by PET (more specifically, a reconstructed image based on list mode data obtained from the PET device).

In addition, it has been found by the inventors through verification experiments 1 and 2 that, according to the present technique (scatter-correction technique in an image space), it is possible to further improve image quality as compared with conventional techniques (scatter-correction technique in a data space). Regarding the reason why the image quality can be improved (more specifically, a reason why scatter components, which are noises, can be removed more effectively) by the present technique as compared with conventional techniques, the inventors have inferred as follows.

The scatter component projection data is considered to be susceptible to spatial variations in the plurality of detectors disposed in the PET device. Therefore, in the interpolated list mode data in the conventional technique, it is considered that influence of the variations in scatter component projection data is emphasized by an interpolation process. Therefore, it is considered that, in the conventional technique, an error (decrease in accuracy) occurs when scatter component projection data is generated. As a result, it is considered that the error is not sufficiently reduced even by correction of the list mode data.

Meanwhile, an image is defined by a plurality of regularly arranged pieces of pixel data, and therefore it is considered that the image is spatially well-ordered data as compared with general numerical data (e.g., list mode data). Therefore, in a case where an interpolation process is carried out in an image space (in a case where a low resolution scatter image is upscaled with the present technique), it is considered to be less susceptible to spatial variations in the plurality of detectors, as compared with a case where an interpolation process is carried out in a data space (a case where scatter component projection data is generated with the conventional technique). As a result, it is considered that, in the present technique, an error occurs relatively less in generating an upscaled scatter image. It is considered that, in the present technique, it is possible to remove scatter components more effectively than in the conventional technique by correcting a current image using such an upscaled scatter image.

Incidentally, it is known that scatter coincidence in a PET device depends on a size of the PET device. Specifically, it is known that, as the size of a PET device decreases, the scatter coincidence tends to increase. Therefore, for example, in a helmet type PET device, influence of a scatter component is larger than in other general PET devices.

However, as described above, according to the present technique, it is possible to effectively remove scatter components from a reconstructed image. Therefore, it is possible to obtain a high quality image even in a case where a helmet type PET device is used. Therefore, it can be said that the present technique is particularly suitable for a helmet type PET device (e.g., the PET device 90). Similarly, the present technique is suitable for a proximity type PET device.

Embodiment 2

Figure 6:
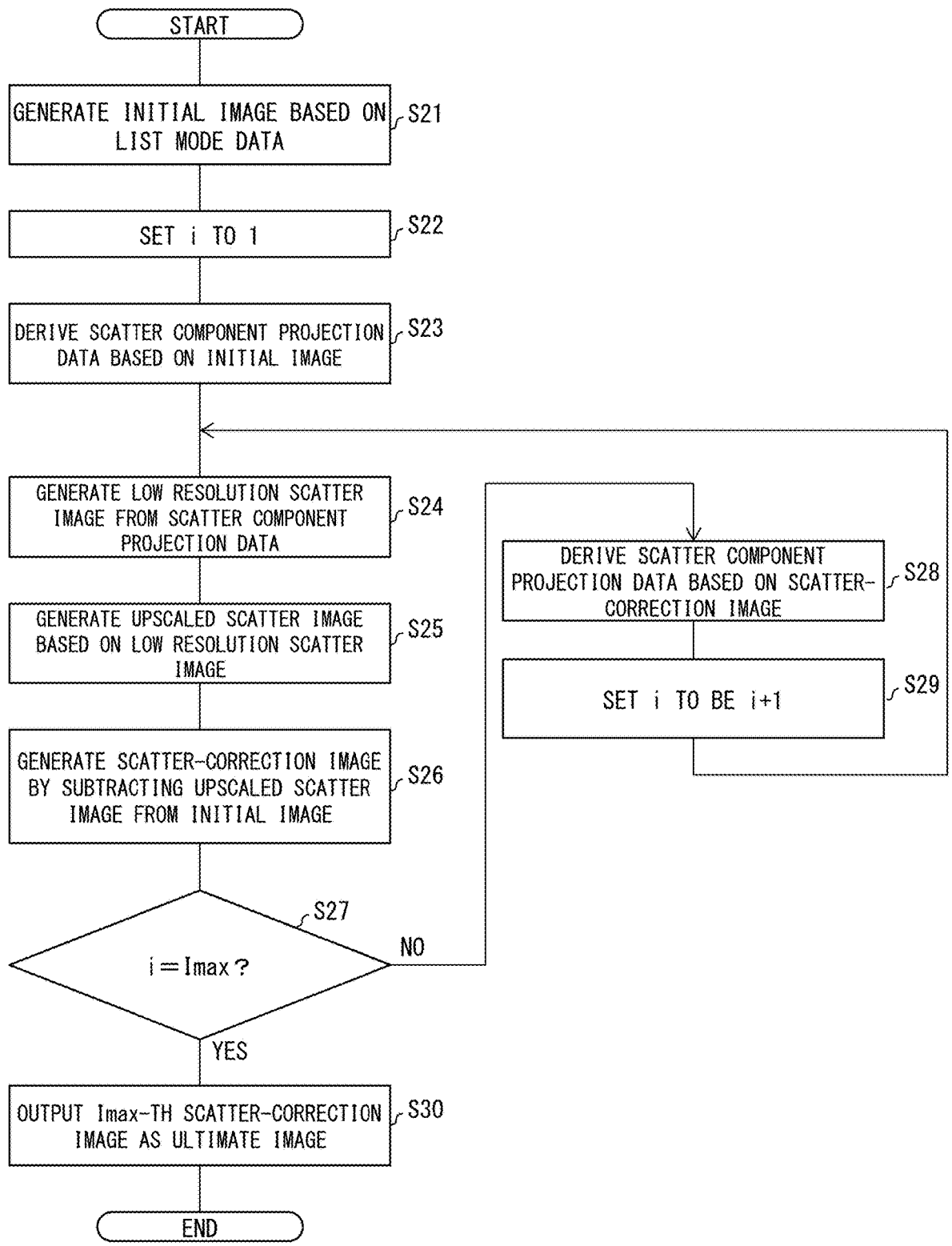
FIG. 6 is a diagram illustrating an example of a process flow of an image processing device in accordance with Embodiment 2.

The process flow of the image processing device 1 is not limited to the example shown in FIG. 2 above. FIG. 6 is a diagram illustrating an example of a process flow of an image processing device 1 in accordance with Embodiment 2. A process of S22 in FIG. 6 is similar to that of S2 in FIG. 2, and therefore a description thereof is omitted here.

First, the first reconstruction process section 11 generates an initial image based on the list mode data (S21). Then, after S22, the scatter component derivation section 12 derives scatter component projection data based on the initial image (S23). S23 corresponds to S8 in a case where of i=1.

Subsequently, the second reconstruction process section 13 reconstructs a low resolution scatter image based on the scatter component projection data (S24). Then, the upscaling process section 14 generates an upscaled scatter image by upscaling the low resolution scatter image (S25).

Subsequently, the image correction section 15 generates a scatter-correction image by subtracting the upscaled scatter image from the initial image (S26). That is, in Embodiment 2, the image correction section 15 generates an image IMGSC(i) as follows: IMGSC(i)=IMG1−IMGUP(i). As such, unlike Embodiment 1, subtraction is carried out with respect to the initial image (IMG1) regardless of the counter value i in Embodiment 2.

Subsequently, the image processing device 1 determines whether or not the value i has reached Imax (S27). In a case where the value i has not reached Imax (No in S27), the scatter component derivation section 12 derives scatter component projection data based on the scatter-correction image (S28). Then, the image processing device 1 increases the value i by 1 (S29).

As such, the scatter component projection data is sequentially updated in accordance with an increase in the value i until the value i reaches Imax. Then, the process returns to S24. That is, the processes of S24 through S29 are recursively repeated until the value i reaches Imax (i.e., until S27 is determined to be Yes). According to such a loop process, scatter components are sequentially removed from the scatter-correction image in accordance with an increase in the value i.

In a case of 1<i<Imax, processes similar to those of S9 and S10 are carried out in S24 and S25 in the current loop (i.e., an i-th loop). Subsequently, in S26, the image correction section 15 newly generates a scatter-correction image (i.e., updates a scatter-correction image generated in the previous loop) by subtracting the upscaled scatter image updated in S25 from the initial image.

After that, in a case where the value i has reached Imax (YES in S27), the image correction section 15 outputs, as an ultimate image, an Imax-th scatter-correction image (i.e., an ultimate scatter-correction image). According to the process of FIG. 6 also, the ultimate image is obtained as an image from which scatter components included in the initial image have been removed. Therefore, Embodiment 2 also brings about an effect similar to that of Embodiment 1.

Note that, in Embodiment 2 also, Imax may be set to 1. That is, in Embodiment 2, it is not necessary that S24 through S29 are recursively repeated. As is clear from FIG. 6, in a case of Imax=1, S28 and S29 are not carried out.

Embodiment 3

In a conventional technique, tail fitting is carried out in a data space. In contrast, according to the image processing device 1, tail fitting can be carried out in an image space. In particular, according to the image processing device 1, tail fitting can be carried out on an entire three-dimensional image, or can be carried out for each slice of the three-dimensional image. Therefore, according to the image processing device 1, it is expected that an error caused by tail fitting can be reduced. The following description will discuss a concept of tail fitting in the image processing device 1, with reference to FIG. 7 and FIG. 8.

Figure 7:
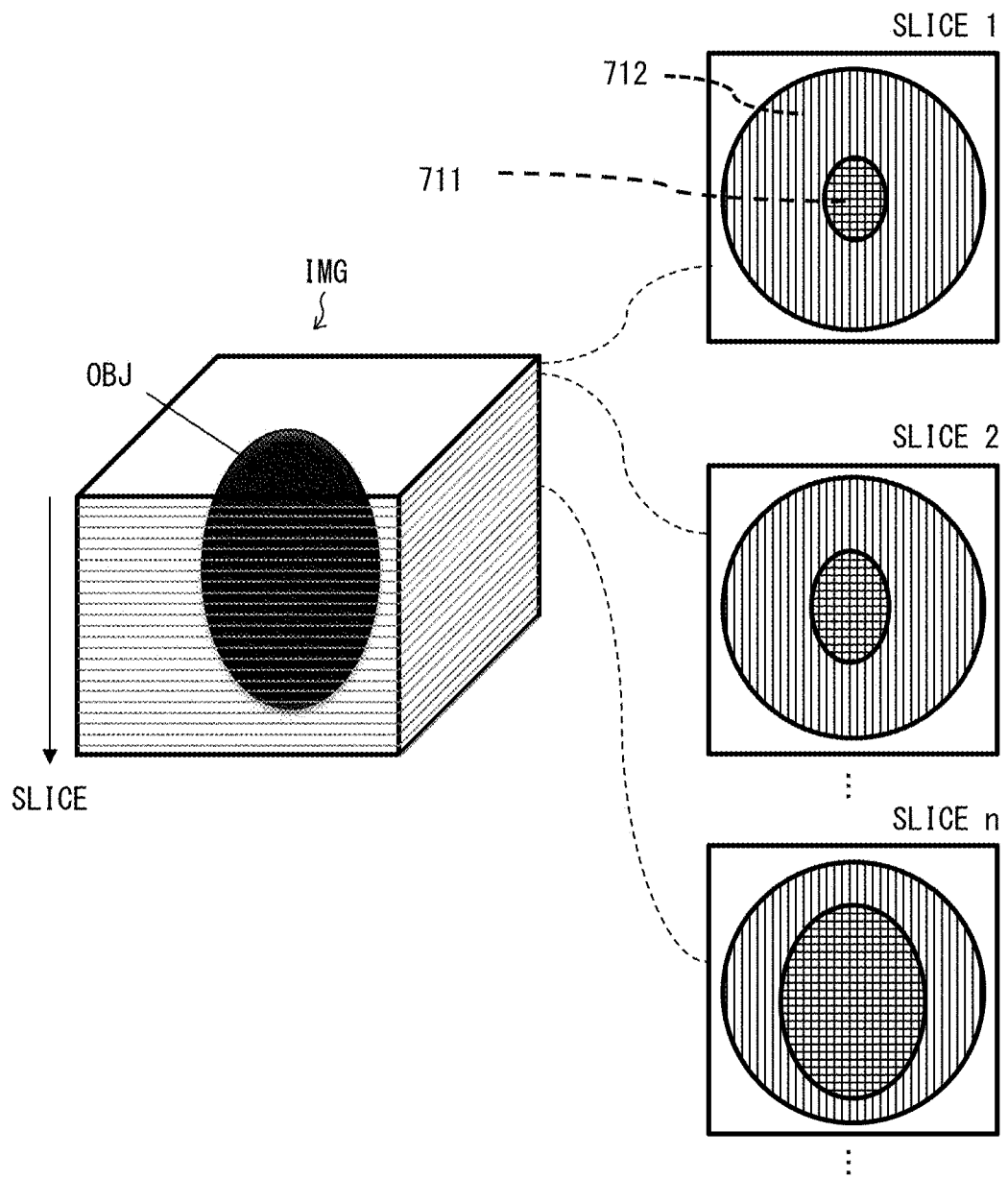
FIG. 7 is a diagram showing an example of a reconstructed image constituted by a plurality of slice images.

FIG. 7 is a diagram illustrating an example of a reconstructed image IMG constituted by a plurality of slice images (two-dimensional images). The image IMG in FIG. 7 is a three-dimensional image in which a figure of an object OBJ is expressed. The object OBJ is another example of the subject in accordance with an aspect of the present invention. A slice n in FIG. 7 is an n-th (e.g., n-th from top) slice image in a stacking direction of the plurality of slice images. The following description will discuss tail fitting with respect to a slice 1 (top slice image), but the description applies similarly to an arbitrary slice n.

As illustrated in FIG. 7, the slice 1 includes an object region 711 (a region in which a figure of the object OBJ is expressed) and a tail region 712 (a peripheral region of the object OBJ). The object region 711 can be extracted by a known technique (e.g., by an extraction technique based on an attenuation coefficient image).

Figure 8:
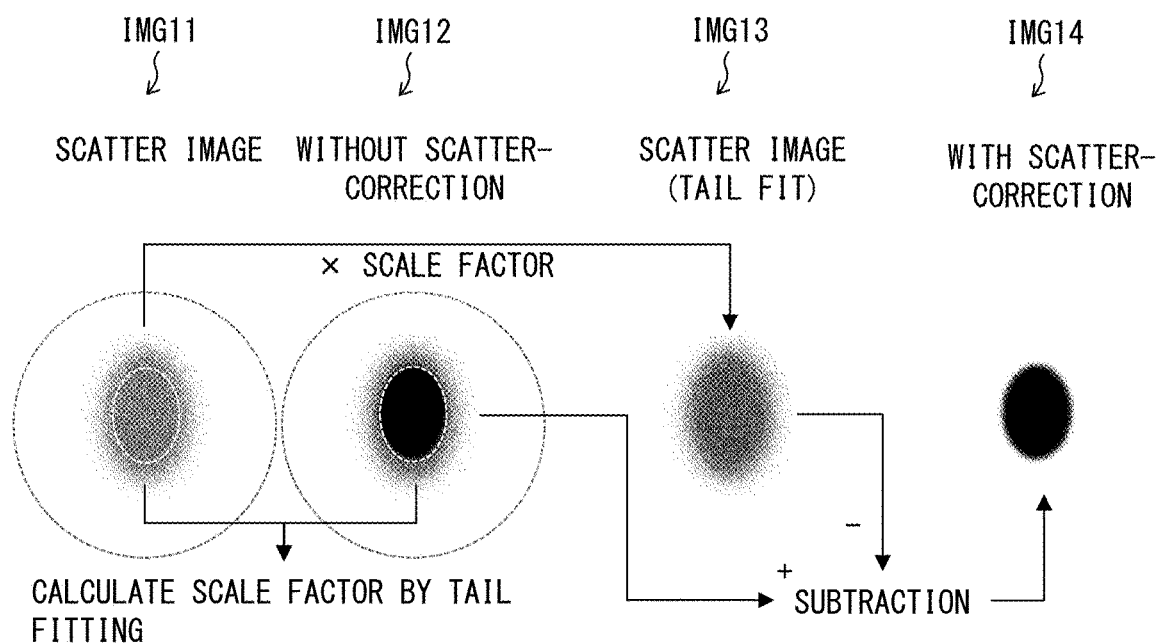
FIG. 8 is a diagram for explaining a flow of a tail fitting process with respect to one slice image.

FIG. 8 is a diagram for explaining a flow of a tail fitting process with respect to one slice image (e.g., slice 1). First, (i) a scatter image IMG11 of the object OBJ and (ii) an image IMG12 of the object OBJ without scatter-correction are generated based on the slice 1. Then, a scale factor c is calculated by carrying out tail fitting based on a known technique based on the image IMG11 and the image IMG12.

Subsequently, a scatter image IMG13 after tail fitting is generated by multiplying the image IMG11 by the scale factor c. The image IMG13 may be referred to also as a tail-fit scatter image. Then, a scatter-correction image IMG14 is generated by subtracting the image IMG13 from the image IMG12. As such, in the image processing device 1, it is possible to remove scatter components of the image IMG12 using the image IMG13.

Embodiment 4

As is clear for a person skilled in the art, the nuclear medicine imaging technique in accordance with an aspect of the present invention is not limited to PET. The nuclear medicine imaging technique need only be a technique that can (i) reconstruct an image based on list mode data and (ii) derive scatter component projection data using scatter estimation simulation.

Another example of the nuclear medicine imaging technique in accordance with an aspect of the present invention is single photon emission-computed tomography (SPECT). Note that list mode data in SPECT is time series data of single counting. As described above, the nuclear medicine imaging device in accordance with an aspect of the present invention is not limited to the PET device, and for example, a SPECT device is also encompassed in the scope of the nuclear medicine imaging device.

[Software Implementation Example]

The functions of the image processing system 100 (hereinafter, referred to simply as "system") can be realized by a program for causing a computer to function as the system, the program causing the computer to function as the control blocks (in particular, the components included in the control section 10) of the system.

In this case, the system includes a computer that has at least one control device (e.g., a processor) and at least one storage device (e.g., a memory) as hardware for executing the program. By executing the program with the control device and the storage device, the functions described in the above embodiments are realized.

The program can be stored in one or more non-transitory computer-readable storage mediums. The storage medium can be provided in the system, or the storage medium does not need to be provided in the system. In the latter case, the program can be supplied to the system via an arbitrary wired or wireless transmission medium.

One or some or all of the functions of the control blocks can be realized by a logic circuit. For example, an integrated circuit in which a logic circuit that functions as the control blocks is formed is also encompassed in the scope of the present invention. Other than those, for example, it is possible to realize the functions of the control blocks by a quantum computer.

Further, each of the processes described in the above embodiments can be executed by artificial intelligence (AI). In this case, the AI may be operated by the control device or may be operated by another device (for example, an edge computer or a cloud server).

ADDITIONAL REMARKS

An aspect of the present invention is not limited to the embodiments described above, but may be altered in various ways by a skilled person within the scope of the claims. Any embodiment based on a proper combination of technical means disclosed in different embodiments is also encompassed in the technical scope of an aspect of the present invention.

REFERENCE SIGNS LIST

1: Image processing device
10: Control section
11: First reconstruction process section
12: Scatter component derivation section
13: Second reconstruction process section
14: Upscaling process section
15: Image correction section
90: PET device (nuclear medicine imaging device)
100: Image processing system
IMG1: Initial image
IMG2: Low resolution scatter image
IMG3: Upscaled scatter image
IMG4: Ultimate image (ultimate scatter-correction image)
PT: Patient (subject)

The invention claimed is:

1. An image processing device, comprising:
a first reconstruction process section that generates, by a reconstruction process with respect to list mode data pertaining to a subject, an initial image indicating a concentration distribution of a radioactive substance in the subject, the list mode data having been acquired by a nuclear medicine imaging device;
a scatter component derivation section that derives, from the initial image, scatter component projection data by scatter estimation simulation, the scatter component projection data indicating a scatter component of radiation rays radiated from the radioactive substance;
a second reconstruction process section that generates a low resolution scatter image by a reconstruction process with respect to the scatter component projection data, the low resolution scatter image indicating the scatter component and having a resolution lower than that of the initial image;
an upscaling process section that generates an upscaled scatter image by upscaling the low resolution scatter image, the upscaled scatter image having a resolution identical with that of the initial image; and
an image correction section that generates a scatter-correction image by subtracting the upscaled scatter image from the initial image.

2. The image processing device as set forth in claim 1, wherein:
the first reconstruction process section updates a current image related to the initial image based on the list mode data;
the image correction section generates a provisional scatter-correction image by subtracting the upscaled scatter image, which has been previously generated, from the current image, which has been updated;
the scatter component derivation section updates the scatter component projection data, which has been previously derived, by newly deriving scatter component projection data from the provisional scatter-correction image by the scatter estimation simulation;
the second reconstruction process section updates the low resolution scatter image, which has been previously generated, by newly generating a low resolution scatter image by a reconstruction process with respect to the scatter component projection data, which has been updated;
the upscaling process section updates the upscaled scatter image, which has been previously generated, by newly generating an upscaled scatter image by upscaling the low resolution scatter image, which has been updated; and
the image correction section updates the scatter-correction image, which has been previously generated, by newly generating a scatter-correction image by subtracting the upscaled scatter image, which has been updated, from the current image, which has been updated.

3. The image processing device as set forth in claim 1, wherein:
the scatter component derivation section updates the scatter component projection data, which has been previously derived, by newly deriving, by the scatter estimation simulation, scatter component projection data from the scatter-correction image, which has been previously generated;
the second reconstruction process section updates the low resolution scatter image, which has been previously generated, by newly generating a low resolution scatter image by a reconstruction process with respect to the scatter component projection data, which has been updated;
the upscaling process section updates the upscaled scatter image, which has been previously generated, by newly generating an upscaled scatter image by upscaling the low resolution scatter image, which has been updated; and
the image correction section updates the scatter-correction image, which has been previously generated, by newly generating a scatter-correction image by subtracting the upscaled scatter image, which has been updated, from the initial image.

4. The image processing device as set forth in claim 1, wherein:
the image correction section outputs an ultimate scatter-correction image which has been obtained as a result of recursive updates carried out a predetermined upper limit number of updates.

5. The image processing device as set forth in claim 1, wherein:
the scatter component derivation section carries out the scatter estimation simulation using a single scatter simulation (SSS) method.

6. An image processing system, comprising:
an image processing device recited in claim 1; and
the nuclear medicine imaging device.

7. The image processing system as set forth in claim 6, wherein:
the nuclear medicine imaging device is a positron emission tomography (PET) device.

8. The image processing system, as set forth in claim 7, wherein:
the PET device is a helmet type PET device.

9. An image processing method in which steps are carried out by a computer, said image processing method comprising:
- a first reconstruction process step of generating, by a reconstruction process with respect to list mode data pertaining to a subject, an initial image indicating a concentration distribution of a radioactive substance in the subject, the list mode data having been acquired by a nuclear medicine imaging device;
- a scatter component derivation step of deriving, from the initial image, scatter component projection data by scatter estimation simulation, the scatter component projection data indicating a scatter component of radiation rays radiated from the radioactive substance;
- a second reconstruction process step of generating a low resolution scatter image by a reconstruction process with respect to the scatter component projection data, the low resolution scatter image indicating the scatter component and having a resolution lower than that of the initial image;
- an upscaling process step of generating an upscaled scatter image by upscaling the low resolution scatter image, the upscaled scatter image having a resolution identical with that of the initial image; and
- an image correction step of generating a scatter-correction image by subtracting the upscaled scatter image from the initial image.

* * * * *